US009724422B2

(12) United States Patent
Hartwig et al.

(10) Patent No.: US 9,724,422 B2
(45) Date of Patent: Aug. 8, 2017

(54) HUMAN LACTOFERRIN DERIVED PEPTIDE FOR USE AS AN ANTIGEN MASKING AGENT

(75) Inventors: Benedikt Hartwig, Darmstadt (DE); Juan Tome Alcalde, Madrid (ES); Norbert Windhab, Hofheim (DE); Maria del Pilar Ansuategui Panzano, Madrid (ES); Matias Javier Vara Carrera, Toledo (ES)

(73) Assignee: Evonik Roehm GmbH, Darmstadt (DE)

( * ) Notice: Subject to any disclaimer, the term of this patent is extended or adjusted under 35 U.S.C. 154(b) by 858 days.

(21) Appl. No.: 13/988,829

(22) PCT Filed: Nov. 26, 2010

(86) PCT No.: PCT/EP2010/068302
§ 371 (c)(1),
(2), (4) Date: Jul. 29, 2013

(87) PCT Pub. No.: WO2012/069089
PCT Pub. Date: May 31, 2012

(65) Prior Publication Data
US 2013/0302342 A1    Nov. 14, 2013

(51) Int. Cl.
| C07K 14/00 | (2006.01) |
| C07K 14/435 | (2006.01) |
| C07K 14/79 | (2006.01) |
| A61K 38/16 | (2006.01) |
| A61K 38/40 | (2006.01) |
| A61K 47/42 | (2017.01) |
| A61K 47/48 | (2006.01) |
| A61K 38/00 | (2006.01) |

(52) U.S. Cl.
CPC ............ *A61K 47/42* (2013.01); *A61K 47/483* (2013.01); *C07K 14/79* (2013.01); *A61K 38/00* (2013.01); *A61K 38/16* (2013.01); *A61K 38/40* (2013.01); *C07K 14/435* (2013.01)

(58) Field of Classification Search
CPC ........ A61K 38/00; A61K 38/40; A61K 38/10; A61K 38/16; C07K 14/79; C07K 14/47; C07K 2319/00; C07K 2319/31
See application file for complete search history.

(56) References Cited

U.S. PATENT DOCUMENTS

| 6,066,469 | A * | 5/2000 | Kruzel | A01N 63/02 435/255.1 |
| 6,423,509 | B1 | 7/2002 | Sung et al. | |
| 2004/0137536 | A1 | 7/2004 | Boone et al. | |
| 2004/0176276 | A1 | 9/2004 | Varadhachary et al. | |
| 2007/0259007 | A1* | 11/2007 | Kruzel | A61K 45/06 424/278.1 |
| 2009/0011038 | A1 | 1/2009 | Seiler et al. | |
| 2009/0318334 | A1 | 12/2009 | Varadhachary et al. | |
| 2010/0061932 | A1 | 3/2010 | Brock et al. | |
| 2013/0108662 | A1 | 5/2013 | Brock et al. | |

FOREIGN PATENT DOCUMENTS

| CN | 101395180 A | 3/2009 |
| EP | 1 905 831 A2 | 4/2008 |
| JP | 2000-45182 A | 2/2000 |
| JP | 2002-520045 A | 7/2002 |
| JP | 2009-512722 A | 3/2009 |
| JP | 2009-521908 A | 6/2009 |
| RU | 2 165 769 C1 | 4/2001 |
| WO | 2004 052305 | 6/2004 |
| WO | 2007 048599 | 5/2007 |
| WO | 2007 076904 | 7/2007 |

OTHER PUBLICATIONS

Bork, P. Powers and pitfalls in sequence analysis: the 70% hurdle. Genome Res 10: 398-400, 2000.*
Bork et al. Go hunting in sequence databases but watch out for the traps. Trends in Genetics. 12(10): 425-427, 1996.*
Brenner, S.E. Errors in genome function. Trends in Genetics 15(4): 132-133, 1999.*
Doerks et al. Protein annotation: detective work for function prediction. Trends in Genetics 14(6): 248-250, 1998.*
Elass et al. Lactoferrin inhibits the lipopolysaccharide-induced expression and proteoglycan-binding ability of interleukin-8 in human endothelial cells. Infection Immunity 70(4): 1860-1866, 2002.*
Levay et al. Lactoferrin: a general review. Haematologica 80: 252-267, 1995.*
Lonnderdal et al. Lactoferrin: molecular structure and biological function. Annu Rev Nutr 15: 93-110, 1995.*
Ngo et al. Computational complexity, protein structure prediction, and the Levinthal paradox. The Protein Folding Problem and Tertiary Structure Prediction, pp. 492-495, 1994.*
Skolnick et al. From genes to protein structure and function: novel applications of computational approaches in the genomic era. Trends in Biotech 18(1): 34-39, 2000.*
Smith et al. The challenges of genome sequence annotation or "The devil is in the details". Nature Biotech 15: 1222-1223, 1997.*
Tokuriki et al. Stability effects of mutations and protein evolvability. Curr Opin Structural Biol 19: 596-604, 2009.*
Wells. J.A. Additivity of mutational effects in proteins. Biochemistry 29 (37): 8509-8517, 1990.*

(Continued)

*Primary Examiner* — Bridget E Bunner
(74) *Attorney, Agent, or Firm* — Oblon, McClelland, Maier & Neustadt, L.L.P.

(57) ABSTRACT

The invention refers to a human lactoferrin derived peptide for use as an antigen masking agent in the production of a pharmaceutical composition for delivery of a biological active substance in a mammalian organism, where the biological active substance is able to induce an undesired immune response by the mammalian organism, where the pharmaceutical composition comprises a supramolecular aggregate of the biological active substance and the human lactoferrin derived peptide, with the effect that after delivery of pharmaceutical composition to the mammalian organism, there is no or only a diminished induction of the undesired immune response against the biological active substance.

15 Claims, 6 Drawing Sheets

(56) References Cited

OTHER PUBLICATIONS

Figure 1:
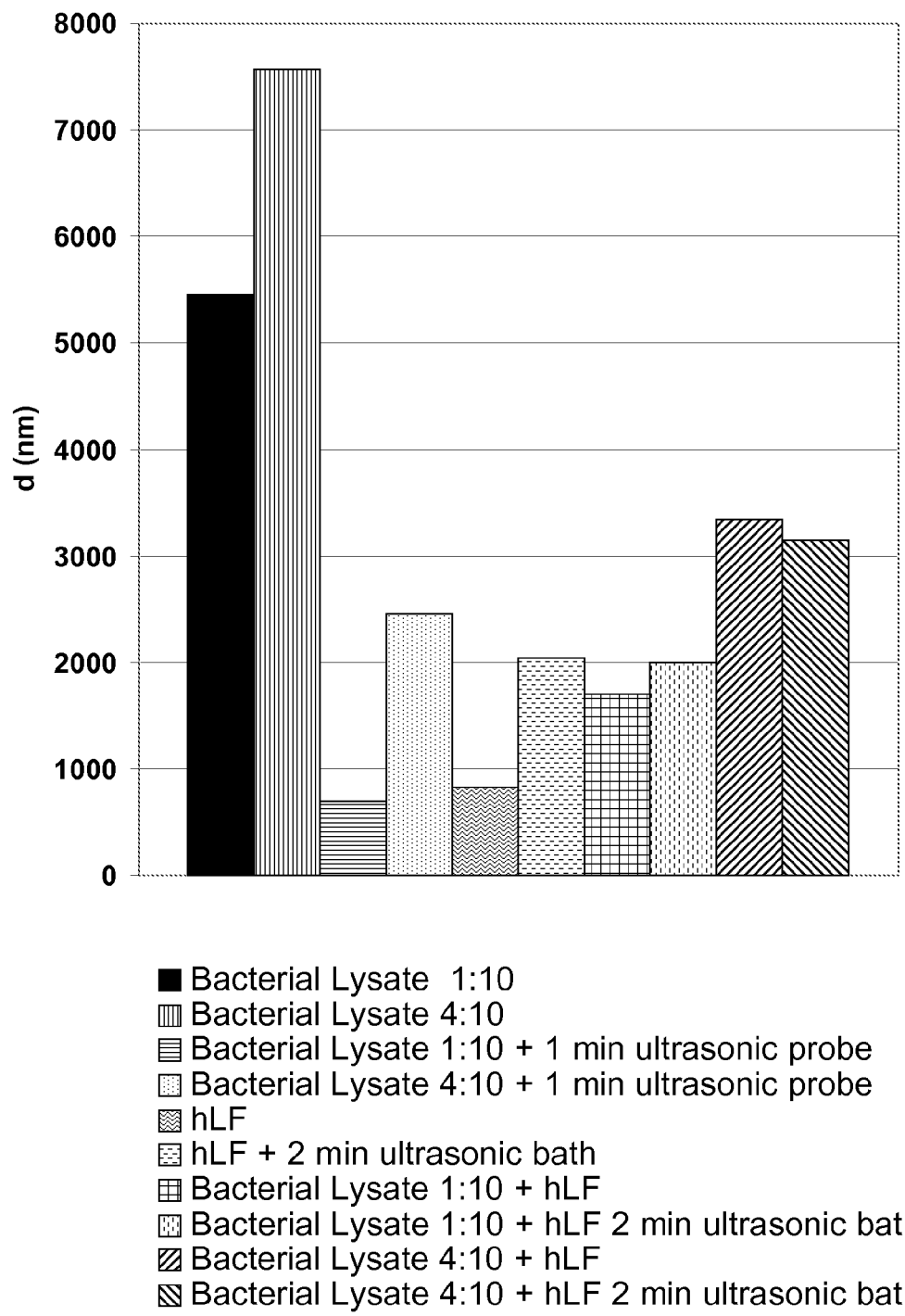

Akhtari et al. Oral human recombinant lactoferrin prevents acute graft-versus-host disease and stimulates reconstitution of donoe bone marrow-derived T-cells in a mouse model of bone marrow transplantation. Biol Blood Marrow Transplant 16(2): S305, #401, Feb. 2010.*

Hwang et al. A novel recombinant human lactoferrin augments the BCG vaccine and protects alveolar integrity upon infection with *Mycobacterium tuberculosis* in mice. Vaccine 27: 3026-3034, 2009.*

Ringden et al. Markedly elevated serum IgE levels following allogeneic and syngeneic bone marrow transplantation. Blood 61(6): 1190-1195, 1983.*

Walkers et al. Increased serum IgE concentrations during infection and graft versus host disease after bone marrow transplantation. J Clin Pathol 37: 460-462, 1984.*

Wasowska et al., Immunobiology of Organ Transplantation (2004) New York: Springer Science+Business Media, pp. 241-264.*

Office Action issued Feb. 9, 2015 in Japanese Patent Application No. 2013-540244 (with English language translation).

Falk Duchardt, et al., "A Cell-penetrating Peptide Derived from Human Lactoferrin with Conformation-dependent Uptake Efficiency" The Journal of Biological Chemistry, vol. 284, No. 52, Dec. 25, 2009, pp. 36099-36108.

Tomita, M., et al., "Twenty-five years of research on bovine lactoferrin applications," Biochimie, vol. 91, No. 1, pp. 52-57, (Jan. 1, 2009) XP 025869227.

International Search Report Issued May 16, 2011 in PCT/EP10/68302 Filed Nov. 26, 2010.

Russian Office Action issued Mar. 5, 2015 in Patent Application No. 2013128884/10 (043019) (with English Translation).

Singer M. et al., "Genes and Genomes, 2 vol., vol. 1, transl. from English, Moscow, 1998, 373 pp, see p. 113, para. 1", 1998, 7 pages. (with English translation).

Combined Chinese Office Action and Search Report issued Apr. 1, 2015 in Patent Application No. 201080070362.8 (with English language translation).

U.S. Appl. No. 13/648,846, filed Oct. 10, 2012, Seiler, et al.

Russian Office Action issued Nov. 7, 2013 in Patent Application No. 2013128884/10 (043019) with English language translation.

Andrew A. Pakula, et al., "Genetic Analysis of Protein Stability and Function", Annu. Rev. Genet, No. 23, (1989), pp. 289-310, in particular pp. 305-306.

U.S. Appl. No. 14/955,696, filed Dec. 1, 2015, Brock et al.

U.S. Appl. No. 14/357,322, Non-Final Rejection, Dec. 13, 2016.

* cited by examiner

- Bacterial Lysate 1:10
- Bacterial Lysate 4:10
- Bacterial Lysate 1:10 + 1 min ultrasonic probe
- Bacterial Lysate 4:10 + 1 min ultrasonic probe
- hLF
- hLF + 2 min ultrasonic bath
- Bacterial Lysate 1:10 + hLF
- Bacterial Lysate 1:10 + hLF 2 min ultrasonic bath
- Bacterial Lysate 4:10 + hLF
- Bacterial Lysate 4:10 + hLF 2 min ultrasonic bath

- Bacterial Lysate 1:10
- Bacterial Lysate 1:10 + 1 min ultrasonic probe
- Bacterial Lysate 4:10
- Bacterial Lysate 4:10 + 1 min ultrasonic probe
- hLF
- hLF + 2 min ultrasonic bath
- Bacterial Lysate 1:10 + hLF
- Bacterial Lysate 1:10 + hLF 2 min ultrasonic bath
- Bacterial Lysate 4:10 + hLF
- Bacterial Lysate 4:10 + hLF 2 min ultrasonic bath

SEQUENCE LISTING

<160> NUMBER OF SEQ ID NOS: 6

<210> SEQ ID NO 1
<211> LENGTH: 22
<212> TYPE: PRT
<213> ORGANISM: Homo sapiens

<400> SEQUENCE: 1

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 2
<211> LENGTH: 18
<212> TYPE: PRT
<213> ORGANISM: Homo sapiens

<400> SEQUENCE: 2

Cys Phe Gln Trp Gln Arg Asn Met Arg Lys Val Arg Gly Pro Pro Val
1               5                   10                  15

Ser Cys

<210> SEQ ID NO 3
<211> LENGTH: 16
<212> TYPE: PRT
<213> ORGANISM: Homo sapiens

<400> SEQUENCE: 3

Phe Gln Trp Gln Arg Asn Met Arg Lys Val Arg Gly Pro Pro Val Ser
1               5                   10                  15

<210> SEQ ID NO 4
<211> LENGTH: 11
<212> TYPE: PRT
<213> ORGANISM: Homo sapiens

<400> SEQUENCE: 4

Phe Gln Trp Gln Arg Asn Met Arg Lys Val Arg
1               5                   10

<210> SEQ ID NO 5
<211> LENGTH: 22
<212> TYPE: PRT
<213> ORGANISM: Homo sapiens

<400> SEQUENCE: 5

Lys Cys Arg Arg Trp Gln Trp Arg Met Lys Lys Leu Gly Ala Pro Ser
1               5                   10                  15

Ile Thr Cys Val Arg Arg
            20

<210> SEQ ID NO 6
<211> LENGTH: 18
<212> TYPE: PRT
<213> ORGANISM: Homo sapiens

<400> SEQUENCE: 6

Cys Arg Arg Trp Gln Trp Arg Met Lys Lys Leu Gly Ala Pro Ser Ile
1               5                   10                  15

Thr Cys

HUMAN LACTOFERRIN DERIVED PEPTIDE FOR USE AS AN ANTIGEN MASKING AGENT

TECHNICAL BACKGROUND

General knowledge about Immunoglobulin G: Immunoglobulin G (IgG) are antibody molecules. IgG is the most abundant immunoglobulin and is approximately equally distributed in blood and in tissue fluids, constituting the main portion of serum immunoglobulins in mammalian animals and in humans. IgG molecules are synthesized and secreted by plasma B cells.

IgG antibodies are predominantly involved in the secondary immune response. The presence of specific IgG generally corresponds to maturation of the antibody response. IgG is the only antibody isotype that can pass through the human placenta, thereby providing protection to the foetus in the uterus. Along with IgA secreted in the breast milk, residual IgG absorbed through the placenta provides the neonate with humoral immunity before its own immune system develops.

IgG can bind to many kinds of pathogens, for example viruses, bacteria, and fungi, and protects the body against them by agglutination and immobilization, complement activation (classical pathway), opsonization for phagocytosis and/or neutralization of their toxins. It also plays an important role in Antibody-dependent cell-mediated cytotoxicity (ADCC).

The mammalian IgG generating immune responses are strongly connected with others and immune response cascades and signalling pathways. So that hapten or immunogen motives and receptors, and receptor families correlate and regulate in many known and un-known ways in mammalian individuals, individually.

This is why any biologically active agent introduced as a therapeutic agent may introduce immune response, desired and undesired even after many individual dosages.

WO 2007/048599 describes particulate drug delivery systems based on a polymeric carrier, characterized in that at least one signal substance for transport through a biological barrier and at least one active ingredient are included, with carrier, signal substance and active ingredient showing no covalent linkages with one another. The signal substance is lactoferrin or a peptide derived from lactoferrin.

In a particularly preferred embodiment, a signal peptide is selected from the group of peptides having an amino acid sequence

```
                                          (SEQ ID NO: 1)
KCFQWQRNMRKVRGPPVSCIKR,
(SEQ ID NO: 3 in WO 2007/048599)

(SEQ ID NO: 2)
CFQWQRNMRKVRGPPVSC,
(SEQ ID NO: 4 in WO 2007/048599)

(SEQ ID NO: 3)
FQWQRNMRKVRGPPVS,
(SEQ ID NO: 5 in WO 2007/048599)

(SEQ ID NO: 4)
FQWQRNMRKVR,
(SEQ ID NO: 6 in WO 2007/048599)

(SEQ ID NO: 5)
KCRRWQWRMKKLGAPSITCVRR
(SEQ ID NO: 29 in WO 2007/048599)
and (SEQ ID NO: 6)
CRRWQWRMKKLGAPSITC
(SEQ ID NO: 30 in WO 2007/048599)
``` or a derivative thereof.

In a preferred embodiment, the cell-penetrating peptides of WO 2007/048599 are comprising an amino acid sequence as shown in SEQ ID NOS: 3, 4, 29 or 30 of WO 2007/048599 or a corresponding sequence with an identity of at least 40%, preferably of at least 50%, particularly preferably with an identity of more than 75% or better of more than 90%.

WO 2007/076904A1 describes a peptide having an amino acid sequence comprising at least 8 consecutive amino acids of the human lactoferrin protein or of the bovine lactoferrin protein, whereby the peptide is suitable to act as a cell-penetrating peptide. Many of the peptides mentioned in WO 2007/076904A1 and in WO 2007/048599 are identical.

The most promising cell-penetrating peptide in WO 2007/076904A1 with the best effects in the examples is KCFQWQRNMRKVRGPPVSCIKR (SEQ ID NO: 3 in WO 2007/076904A1, SEQ ID NO: 1 herein).

The lactoferrin derived cell-penetrating peptides are intended to permit the transport of cargo molecules, which are active pharmaceutical ingredients such as DNA, RNA, peptides or antigens for vaccination, which may be orally ingested, through the biological membranes and thus allow efficient uptake of these molecules in the human or animal organism.

Problem and Solution

When a biological active substance which is delivered to a mammalian organism in order to cure a disease induces an undesired immune response this may become a serious problem, when the same biological active substance has to be delivered later on to that certain organism once again.

It was an object of the present invention to find an antigen masking agent which can be used as an adjuvant or as an excipient in the production of a pharmaceutical composition for delivery of a biological active substance in a mammalian organism, where the biological active substance is able to induce an undesired immune response by the mammalian organism, with the effect that after delivery of pharmaceutical composition to the mammalian organism, there is no or only a diminished induction of the undesired immune response against the biological active substance.

The problem is solved by a human lactoferrin derived peptide for use as an antigen masking agent in the production of a pharmaceutical composition for delivery of a biological active substance in a mammalian organism, where the biological active substance is able to induce an undesired immune response by the mammalian organism, where the pharmaceutical composition comprises a supramolecular aggregate of the biological active substance and the human lactoferrin derived peptide, with the effect that after delivery of the pharmaceutical composition to the mammalian organism, there is no or only a diminished induction of the undesired immune response against the biological active substance.

DETAILS OF THE INVENTION

The invention refers to a human lactoferrin derived peptide for use as an antigen masking agent in the production of a pharmaceutical composition for delivery of a biological active substance in a mammalian organism, where the biological active substance alone is able to induce an undesired immune response by the mammalian organism, where the pharmaceutical composition comprises a conjugate of the biological active substance and the human lactoferrin derived peptide, with the effect that after delivery of the pharmaceutical composition to a or to the mammalian organism, there is no or only a diminished induction of the undesired immune response against the biological active substance.

Since the human lactoferrin derived peptide is derived from human lactoferrin it is not immunogenic to the human immunogenic system.

Surprisingly the human lactoferrin derived peptide it is not or only to a low extent immunogenic to the immunogenic system of mammalian animals, preferably to production animals or to domestic animals, like for instance pigs, sheep, cows or dogs used as model species in the development of drugs although the sequences are genetically not conserved. Thus the benefits of the present invention are not limited to application in man but may also be applied to veterinarian applications and the development of human therapies using animal models.

Human Lactoferrin Derived Peptide

The human lactoferrin derived peptide may have a length of 19 to 30 amino acids.

The human lactoferrin derived peptide may have a length of 19 to 30 amino acids and may include an amino acid sequence of KCFQWQRNMRKVRGPPVSCIKR (SEQ ID NO: 1) or a sequence which is at least 90, 95 or 98% homologous to SEQ ID NO: 1.

The human lactoferrin derived peptide is preferably a peptide with an amino acid sequence of KCFQWQRNMRKVRGPPVSCIKR (SEQ ID NO: 1) or a sequence which is at least 90, 95 or 98% homologous to that sequence.

Most preferably the human lactoferrin derived peptide is at least 90, 95 or 98% homologous to SEQ ID NO: 1 and where the cysteine residues in positions 2 and 19 are present. Preferably the cysteine residues are present in oxidized form, forming an internal Cys-Cys-bridge.

Any additional standard chemical modification used in peptide GMP-synthesis such as N-acetylation, acylation, methylation, benzylation, C-amidation, esterification, C-terminal-bulkesters, isosteric amino-acid modifications and non-natural amino-acids such as thiophenyl-alaline or cycloproline-alanine or any other aminoacid substitution with amid-, ester, or ether-backbone may be included.

However it is preferred that, except for the formation of the internal Cys-Cys-bridge, the human lactoferrin derived peptide will show no additional chemical modifications.

Biological Active Substance which is Able to Induce an Undesired Immuno-Response by a Mammalian Organism A biological active substance which is able to induce an undesired immune response by a mammalian organism is usually comprised or contained in a pharmaceutical form or in a pharmaceutical preparation.

Biological active substance substances which are intended to be used to induce a desired immune response by the mammalian organism, for example most vaccines, are not under the scope of the definition "undesired immune response".

The biological active substance which is able to induce an undesired immune response by the mammalian organism may be preferably selected from the group of biological active proteins or biological active peptides, antisera, polyclonal or monoclonal antibodies. Also to be named are recombinant proteins providing other "soluble receptors" or soluble receptor binders" or modified recombinant proteins like polyethylen gylcol(PEG)-ylated entities as well as therapeutic agents with the risk of immunogeneicity as undesired side effect including small molecules where such risk is known or potentially relevant like antibiotics, peptide-drugs and peptide-mimetics.

The biological active substance which is able to induce an undesired IgG immune response may be comprised in a sample of blood which is transfused to a mammalian organism.

The biological active substance which is able to induce an undesired IgG immune response is comprised in or on the surface of an organ which is transplanted to a mammalian organism.

Undesired Immune Response

An undesired immune response by the mammalian organism is the response of the immune system by production of antibodies against a biological active substance which is delivered to a mammalian organism in order to exert a desired beneficial therapeutic effect which is different from a immune response or in which the immune response in an undesired side effect.

The undesired immune response may be (prevailing) an IgG immune response.

The undesired immune response may be (prevailing) an IgE immune response.

Even if the undesired immune response may not cause undesired side effects at the first delivery of that pharmaceutical form or in a pharmaceutical preparation comprising or containing the biological active substance which is able to induce the undesired immune response, the undesired immune response may cause undesired side effects when the pharmaceutical preparation comprising or containing the biological active substance which is able to induce the undesired (IgG or IgE) immune response is or has to be delivered a second time or another time or several times or over a period of time. In this case for instance existing IgG-levels in the plasma may partially or fully inactivate the biological active substance and diminish its desired therapeutical effect. In some cases the partially or fully inactivation of the biological active substance may also go hand in hand with irritations, fever or other undesired side effects. These side effects may be induced unspecifically by the presence of the IgG-antibody aggregates or precipitates with the biological active substance.

Typical examples of a biological active substance which is able to induce an undesired IgG immune response by a mammalian organism are for instance: Anti-venom-antisera against the venom of venomous animals. For instance snakes, insects, spiders or certain jellyfish species, where the anti-sera are produced by animals, usually by horses, where the anti-sera are intended to cure a human being who had contact with that venom. After the first delivery of that anti-serum the individual human being usually develops an undesired prevailing IgG immune response against the horse proteins, mainly horse IgG-antibodies comprised in that anti-serum.

Well known is the case of specific anti-snake-venom antisera produced by horses, which when they are delivered to a human which have been bitten by the certain snake species in order to cure the severe effects of the snake venom. After the first delivery of the anti-snake-venom antiserum, the individual person may be cured by the inactivation of the venom but may develop an undesired IgG immune response against the horse proteins, mainly horse IgG-antibodies comprised in that serum. When the same person is later on bitten by the same or another snake treating him with horse anti-snake-venom antisera again may be dangerous because of the present level of IgG antibodies developed against the horse serum proteins.

Known are also immunomodulatory therapies of human low-risk myelodysplastic syndromes where anti-lymphocyte/antithymo-lymphocyte globulins are employed. In these therapies globulins with antibodies directed against human immunogenic cells which are produced in rabbits or in horses are delivered to the human patient over a certain period of time. Also in this case there is the danger of undesired IgG immune-response against the rabbit or horse proteins, mainly horse IgG antibodies, comprised in that globulin fractions. This undesired IgG immune response may negatively influence the present or a repeated therapy.

Known is further the application of pharmaceutical preparations comprising or containing monoclonal antibodies raised against epitopes on cancer cells.

Other cases where the suppression of an undesired IgG immune response in the sense of the invention may be beneficial may be the field of blood transfer, where incompatibilities between the transfused blood and the immune system of the patient in the sense of undesired IgG immune response may occur.

Another case where the suppression of an undesired IgG immune response in the sense of the invention may be beneficial may be the field of organ transfer, where incompatibilities between the transferred organ, may it be kidney, liver, lung or heart among other examples, and the immune system of the patient in the sense of undesired IgG immune response may occur and thus may at least partially promote repulsion or rejection reactions.

The biological active substance which is able to induce an undesired IgG immune response by the mammalian organism thus may comprise pharmacological or biological active proteins or peptides, especially proteins or peptides which are not native to the mammalian organism to which they are delivered.

Not native may mean that the biological active proteins or peptides originate either from another species, preferably from another mammalian species, in comparison to which species they are delivered, or from the same species or of semisynthetic origin.

Not native may mean or that the biological active proteins or peptides where modified in a way that make them detectable by the IgG-immune-response of the mammalian organism to which they are intended to be delivered.

The preferred mammalian organism to which the biological active substance which is able to induce an undesired IgG-immune-response may be delivered is *Homo sapiens*.

For instance a protein which originates from a certain mammalian organism may become detectable by the IgG-immune-response of that mammalian organism when it was produced by a recombinant microbial organism.

For instance a glycosylated protein originating from a eukaryotic source organism but which was produced in a recombinant prokaryotic organism will usually lack the glycosylation. Thus the recombinant protein may become detectable by the IgG-response of that original source mammalian organism when it is delivered back to that organism in the form of a pharmaceutical preparation.

Side effects in connection with undesired IgE immune response are well known for instance as allergies, anaphylaxis or even as anaphylactical shock.

The biological active substance which is able to induce an undesired IgG or IgE immune response by the mammalian organism may comprise preparations which comprise or consist of antisera or polyclonal or monoclonal antibodies or recombinant proteins providing other "soluble receptors" or soluble receptor binders" or modified recombinant proteins like polyethylen glycol polyethylen glycol(PEG)-ylated, truncated, or genetically modified entities as well as therapeutic agents with the risk of immunogenicity as undesired or critical or lethal side effects such as anaphylaxis and anaphylactic shock including small molecules like antibiotics, anaesthetics where such risk is known as well as any biologically active compound were immunogeneicity is potentially relevant including peptide-drugs and peptide-mimetics, growth- or necrosis factors, or mixtures such as body fluid fractions such as blood factors from human blood or cell cultures.

Furthermore the immunomodulatory effect of human Lactoferrin fragment could be used for antigen masking effects in order to manipulate the potential immune response inducing agents in the field of allergy. For instance the association of human Lactoferrin fragment with pollen, grass-pollen, milk proteins, mellitine, egg proteins etc. could manipulate the allergic reaction of a human organism against these epitopes and antigens.

Pharmaceutical Composition

The human lactoferrin derived peptide may be used as an antigen masking agent in the production of a pharmaceutical composition for delivery of a biological active substance in a mammalian organism.

A pharmaceutical composition may be a pharmaceutical form or preferably multiparticulate pharmaceutical form, preferably selected from pellets, granules, minitablets, tablets or capsules or other pharmaceutical forms. The pharmaceutical composition may also include veterinarian pharmaceutical compositions.

The pharmaceutical composition comprising the human lactoferrin derived peptide and the biological active substance may comprise further excipients, which are known by the skilled person to be useful in the formulation of pharmaceutical forms. Typical excipients are antioxidants, brighteners, binding agents, diluents, fillers, flavouring agents, flow aids, fragrances, glidants, penetration-promoting agents, pigments, plasticizers, polymers, pore-forming agents, solvents or stabilizers.

The pharmaceutical composition may comprise, may comprise essentially or may contain up to 80, up to 50, up to 25, up to 10% by weight or any pharmaceutical excipients, e.g. further excipients, which are known by the skilled person to be useful in the formulation of pharmaceutical forms.

Supramolecular Aggregate

Most preferably the human lactoferrin derived peptide and the biological active substance form a supramolecular aggregate, which may also be called a complex or a conjugate, wherein the human lactoferrin derived peptide and the biological active substance are not covalently bound to each other. In this case the supramolecular aggregate are kept together for instance by ionic forces or by Van-der-Waals forces.

These supramolecular aggregates may be very advantageously prepared by adding to the biological active compound in an aqueous or process media solution or suspension the human lactoferrin derived peptide. This solution has to be mixed gently for a short time, preferably for up to 2 minutes, or incubated for up to 1 hour, up to 2 hours or above.

Beside the human lactoferrin derived peptide and the biological active substance the supramolecular aggregate may additionally comprise or contain a carrier, for example a carrier polymer like a dendritic polymer.

Also possible but less preferred the human lactoferrin derived peptide and the biological active substance form a supramolecular aggregate wherein the human lactoferrin derived peptide and the biological active substance are covalently bound to each other. In this case the supramolecular aggregate may be formed by a chemical reaction of reactive groups in human lactoferrin derived peptide with reactive groups in the biological active substance. Alternative additional chemical reactive linker molecules may be used to connect the molecules.

Preferably the supramolecular aggregates may comprise, may comprise essentially or may contain at least 20%, at least 50% by weight, at least 80%, at least 90% by weight or 100% of the human lactoferrin derived peptide and the biological active substance. The supramolecular aggregate may be a part of a pharmaceutical composition which may comprise further excipients.

Preferably the pharmaceutical composition may comprise, may comprise essentially or may contain at least 20, at least 50 at least 75 at least 90% by weight or 100% of the supramolecular aggregate.

Process for Preparing a Pharmaceutical Composition

The inventions also refers to a process for preparing a pharmaceutical composition as defined herein by mixing the human lactoferrin derived peptide and the biologically active agent under native conditions, incubating the mixture to allow the (covalent or non covalent) formation of a supramolecular aggregate and adding the mixture to the pharmaceutical composition.

In the simplest embodiment the pharmaceutical composition may be identical which said mixture which means that the final pharmaceutical composition essentially only contains the human lactoferrin derived peptide and the biologically active agent. However in many cases it may be advantageous or appropriate to add further pharmaceutical excipients to form the (final) pharmaceutical composition.

Native conditions shall mean conditions under which the biological activity of the human lactoferrin derived peptide and the biologically active agent are maintained. A native condition may be for instance the mixing the human lactoferrin derived peptide and the biologically active agent an aqueous buffer solution for instance phosphate buffered saline, pH 7.4, or in physiological sodium chloride solution.

Incubating the mixture to allow the formation of supramolecular aggregates shall mean enough time to allow for the aggregation of human lactoferrin derived peptide and the biologically active agent. Usually mixing and incubation for up to 2 minutes at room temperature may be sufficient. However incubating for up to 1 hour, up to 2 hours or above may be suitable as well. Suitable temperatures for the formation of supramolecular aggregates may be in the range from 0 and 37° C., preferably 4 to 30° C., room temperature around 18 to 28° C. may be suitable.

EXAMPLES

Example 1

Non-Covalent Coupling of Human Lactoferrin Fragment (hLf) with Bacterial Lysate

Material:

Bacterial lysate from *Escherichia coli*, Human Lactoferrin fragment, KCFQWQRNMRKVRGPPVSCIKR (SEQ ID NO: 1), Phosphate buffered saline, pH=7.4 (Ph. Eur.): 5.97 g of disodium hydrogen phosphate dihydrate (corresponding to 4.76 g of disodium hydrogen phosphate), 0.38 g of potassium dihydrogen phosphate and 16 g of sodium chloride were dissolved in 1.8 l of distilled water. Afterwards the prepared clear solution was given into 2l volumetric flask, filled up to calibration mark with distilled water and subsequently homogenized. Then the pH was adjusted to 7.43 at 23.2° C. using 3 ml of HCl 1 N before filling the final solution in PE bottles.

Device:

Malvern Zetasizer Nano ZS90; Size parameters:

Material: Protein RI: 1.45 Absorption: 0.00, Dispersant: Water 25° C.: 0.8872 cP RI: 1.330; 37° C.: 0.6864 cP RI: 1.330, Cell: DTS 1060C: Clear disposable zeta cell Measurement: Automatic 3 runs, positioning method: seek for optimum position, automatic attention selection, analysis model: general purpose Zeta parameters: Dielectric constant: 78.5 at 25° C. and 74.4 at 37° C.

Model: Smoluchowski F(KA)value: 1.5, measurement: automatic 3 runs Automatic attention selection Sample Preparation Peptide oxidation: The peptide was dissolved to a concentration below 1 mM (2.75 mg/mL) in phosphate buffered saline (PBS), pH 7.4. (Ph. Eur.), e.g., 5 mg in 10 mL (=0.5 mg/mL). The solution was purged with pure oxygen for 5 minutes at 37° C. Incubate for 2 h at 37° C.

For the bacterial lysate dilution 1 mL of bacterial cell lysate were diluted up to 10 mL with PBS pH 7.4. (Ph. Eur.).

Attachment to the lysate particles was achieved by adding 1 ml bacterial lysate (=1.2 mg *E. coli*) with 0.097714286 mg hLF.

20 μL of a 0.5 mg/mL solution of peptide were added to 1 mL of the previously diluted vaccine (0.12 mg/mL) and incubated 2 hours under low stirring, 100-150 rpm, at 4° C., preventing any foam building

TABLE 1 analysed samples and their composition

| SAMPLE | SONICATION | BACTERIAL LYSATE SUSPENSION | OXIDISED HLF FRAGMENT SOLUTION |
|---|---|---|---|
| Bacterial Lysate 1:10 | No | 5 mL 0.12 mg/mL | — |
| Bacterial Lysate 4:10 | 1 min, sonicator probe | 5 mL 0.12 mg/mL | — |
| Bacterial Lysate 1:10 + 1 min ultrasonic probe | No | 5 mL 0.48 mg/mL | — |

TABLE 1-continued analysed samples and their composition

| SAMPLE | SONICATION | BACTERIAL LYSATE SUSPENSION | OXIDISED HLF FRAGMENT SOLUTION |
|---|---|---|---|
| Bacterial Lysate 4:10 + 1 min ultrasonic probe | 1 min, sonicator probe | 5 mL 0.48 mg/mL | — |
| hLF | No | — | 1.5 ml 0.5 mg/mL |
| hLF + 2 min ultrasonic bath | 2 min., sonication bath | — | 1.5 ml 0.5 mg/mL |
| Bacterial Lysate 1:10 + hLF | Pre-sonicated as above | 5 mL 0.12 mg/mL | 200 µl 0.5 mg/mL |
| Bacterial Lysate 1:10 + hLF 2 min ultrasonic bath | Pre-sonicated as above +2 min. sonication bath after hLF attachment | 5 mL 0.12 mg/mL | 200 µl 0.5 mg/mL |
| Bacterial Lysate 4:10 + hLF | Pre-sonicated as above | 5 mL 0.48 mg/mL | 200 µl 0.5 mg/mL |
| Bacterial Lysate 4:10 + hLF 2 min ultrasonic bath | Pre-sonicated as above +2 min. sonication bath after hLF attachment | 5 mL 0.48 mg/mL | 200 µl 0.5 mg/mL |

Figure 2:
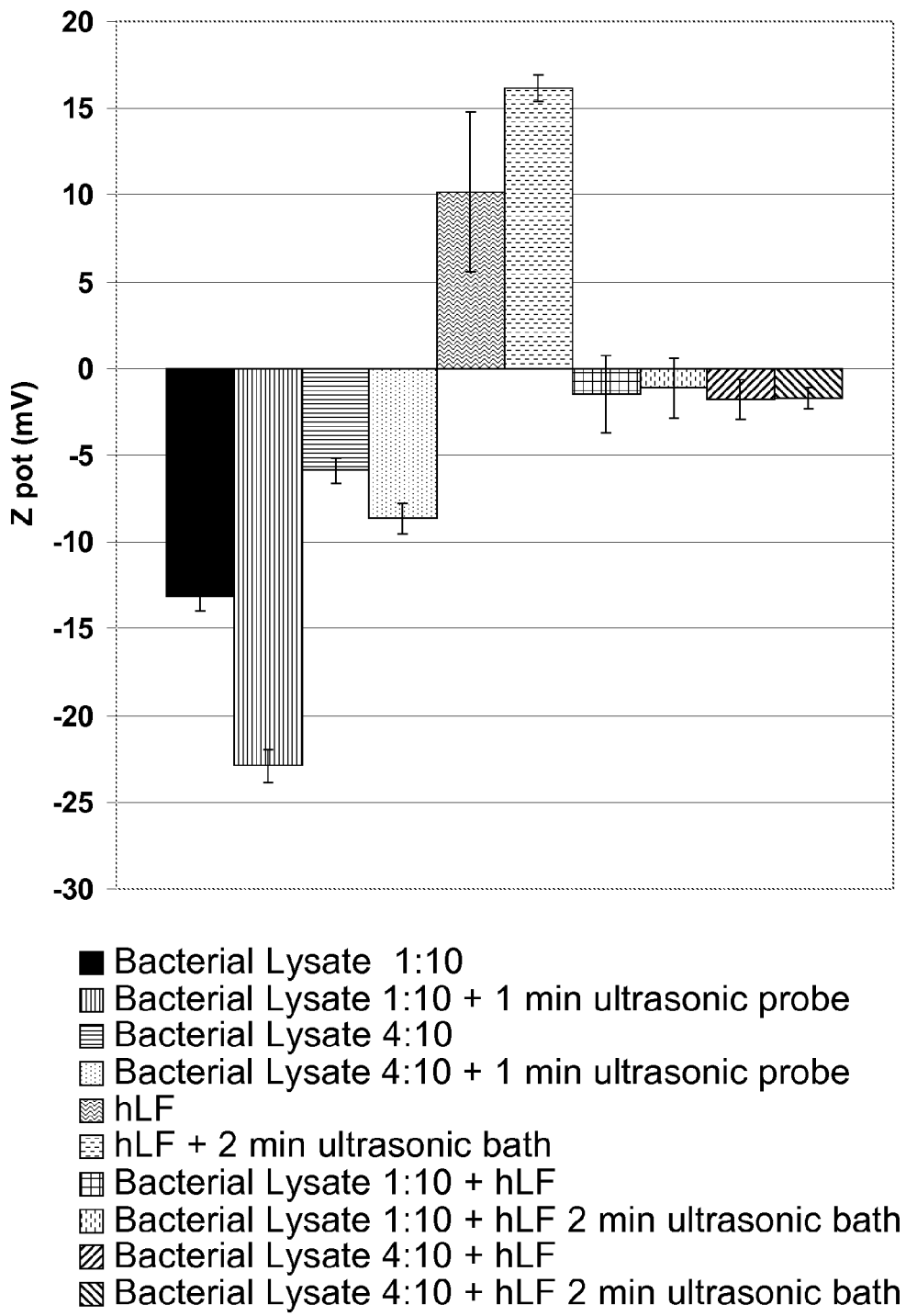

Findings
Zeta Potential (FIG. 2)

It was shown that the *E. coli* lysate is a suspension, consisting of negatively charged surface particles. The hLF peptide fragment, even if formation of aggregates is observed, displays an overall positive charge, and the addition of the second to the first results in a variation of the lysate surface properties.

Particle Size (FIG. 1)

The Figure "particle size" displays the averages

Particle size data point out the findings:

Aggregation is prone to occur in all cases: vaccine alone, hLF fragment alone, and the combination thereof.

These aggregation phenomena led to larger particle sizes

Aggregation and sedimentation can occur, reversed by means of sonication and/or suitable stirring.

Example 2

Immunomodulation of Rat Immune System by Treatment with Antigen, Human Lactoferrin Fragment and Combination of Antigen and Human Lactoferrin Fragment Material Bacterial lysate: *Klebsiella pneumoniae* CECT 141; 12.000 million bacteria/mL (ten times the final concentration), Standard non-glycerinated formulation, without phenol hLF fragment, KCFQWQRNMRKVRGPPVSCIKR (SEQ ID NO: 1) oxidised form, as lyophilisate product; dosed in vials of 50 mg each, in 25 mL vials, to be reconstituted and used as stock solution for the length of the assay. Once reconstituted, keep cooled (4° C.)

Phosphate buffered saline (PBS) Sterilise by any suitable procedure and store in a suitable container when not used immediately after elaboration. Consider its storage at 4° C. for longer periods of time.

Procedures

Reconstitution of the hLF stock solution was performed by reconstitution of the 50 mg hLF fragment in a vial by addition of 20 mL of PBS. It was ensured a complete, proper reconstitution to a clear, homogeneous, particle-free solution. The vial was gently shaken by repeated inversion of the closed vial. The result was the hLF-stock solution for the trial: nominal concentration 2.5 mg/mL.

The hLF dilution for the animal trial was performed daily. For this 1 mL of the reconstituted hLF stock solution were transferred into a new 25 mL vial, followed by adding 21.5 mL of PBS and carefully mixing by repeated inversions of the closed vial to avoid foam formation. The result was the daily stock dilution, nominal concentration 0.1 mg/ml.

"A+B" Formulation 4.5 ml of the daily hLf dilution were transferred to a suitable vial (5 ml capacity or bigger), followed by adding 0.5 ml of the 12,000 million bacteria/mL bacterial lysate, and carefully mixing by repeated inversions of the closed vial to avoid foam formation. The result was 5 ml of A+B vaccine, 1200 million bacteria/ml, 0.1 mg hLf fragment/ml, ensuring the ratio 12:1.

"B" Formulation 4.5 ml of the daily hLf dilution were transferred to a suitable vial (5 ml capacity or bigger), followed by adding 0.5 ml of PBS and carefully mixing by repeated inversions of the closed vial and avoid foam formation. The result was 5 ml of 0.1 mg/ml hLf fragment solution.

"A" Formulation 0.5 ml of the bacterial lysate (12,000 million bacteria/ml) were transferred to a suitable vial (5 ml capacity or bigger), followed by adding 4.5 ml of PBS, and carefully mixing by repeated inversions of the closed vial and avoid foam formation. The result was 5 ml of bacterial lysate, 1200 million bacteria/mL ("A" Bacterial lysate)

Doses and Administration of the Treatments:

"A+B" Administration

Application of 0.5 mL of "A+B" to each of the three rats from group A+B (i.p.).

Application of 0.5 mL of "A+B" to each of the three rats from group α+β (intragastrically).

"B" Administration

Application of 0.5 mL of B to the rats from group B. (i.p.).

Application of 0.5 mL of B to the three from group β (intragastrically).

"A" Administration

Application of 0.5 ml of vaccine A to the three rats from group A Application of 0.5 ml of vaccine A to the three rats from group α

Animal Treatment

Oral lysates of *Klebsiella pneumoniae* CECT 141 were used as model for an inoculum which induces IgG immuno response in rats as model organisms when administered intragastrically or intraperitoneally. The human lactoferrin derived peptide with the amino acid sequence KCFQWQRNMRKVRGPPVSCIKR (SEQ ID NO: 1) was used to form conjugates with the lysates of *Klebsiella pneumoniae* CECT 141 in the following manner:

Six groups of three rats were used a. Group A: Will be administered Bacterial Lysate (Formulation "A") intraperitoneally b. Group B: Will be administered hLf fragment (Formulation "B") intraperitoneally c. Group C: conjugate (Formulation "A+B") will be administered intraperitoneally d. Group α: Will be administered Formulation "A" intragastrically e. Group β: Will be administered Formulation "B" intragastrically f. Group δ: Will be administered Formulation "A+B" intragastrically Duration of the trial: 4 weeks (28 days)

Pattern of Product Application

TABLE 2

Treatment of groups of rats and amount

| Day | A | B | A + B | Control |
|---|---|---|---|---|
| 0 | 0.5 ml | 0.5 ml | 0.5 ml | no dose |
| 7 | 0.5 ml | 0.5 ml | 0.5 ml | no dose |
| 14 | 0.5 ml | 0.5 ml | 0.5 ml | no dose |
| 21 | 0.5 ml | 0.5 ml | 0.5 ml | no dose |

Parameters and Sampling Schedule

The parameter to be measured is total IgG. The method will be performed by ELISA. The sampling schedule for all groups will be as follows (table 3):

TABLE 3

Blood samples would be taken by the following scheme

| Day | Remark |
|---|---|
| 0 | Before administering the dose |
| 6 | |

TABLE 3-continued

Blood samples would be taken by the following scheme

| Day | Remark |
|---|---|
| 13 | |
| 20 | |
| 27 | Sacrifice |

Findings

Variation in the IgG Levels over time

Figure 3:
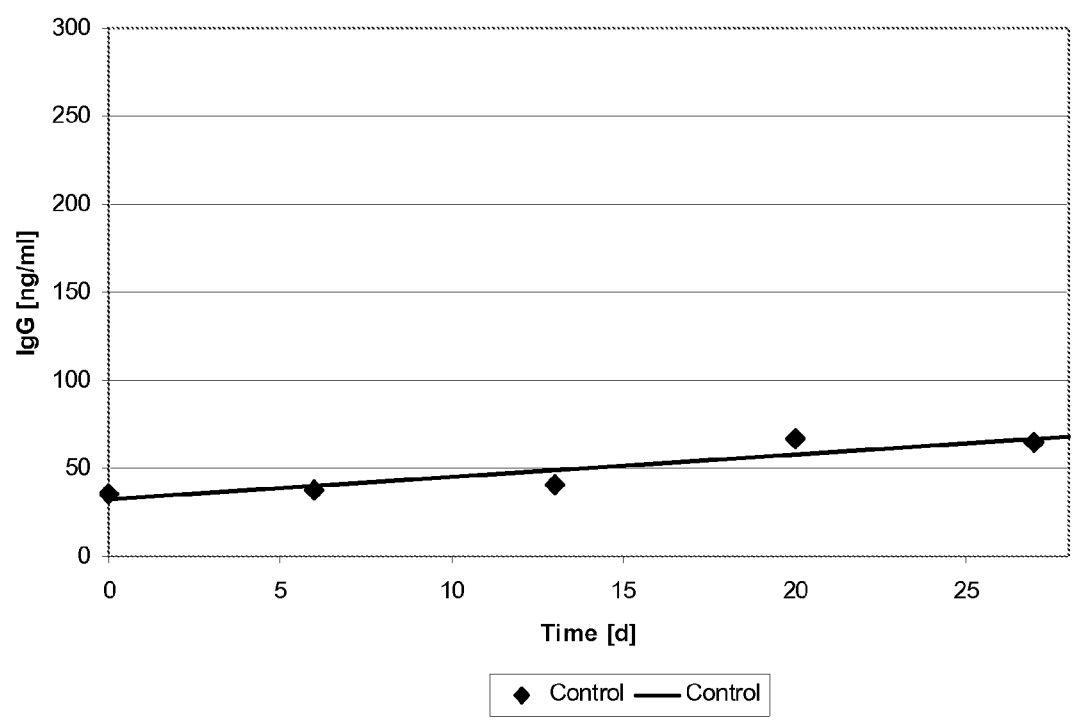

Control Group (FIG. 3)

In the animals of the control group, the IgG levels will be kept constant over time with no statistically significant differences observed between the various times studied Group with Human Lactoferrin (hLf, "B"-Formulation") (FIG. 4):

Treatment with Human Lactoferrin does not appear to induce any effect on IgG levels over time, with no statistically significant differences observed between the IgG levels of the rats undergoing hLf treatment at any of the study times independent of the mode of administration.

Group Treated with Bacterial Extract ("A"-Formulation) (FIG. 5):

In the animals undergoing intraperitoneal treatment with bacterial extract, we observed that the IgG levels tend to increase significantly over time. Additionally, it should be noted that the IgG levels increase with the number of doses of bacterial extract, which means that the effect of this treatment is cumulative, explaining the increase of IgG levels over time. The same behavior is observed in animals treated intragastrically with bacterial extract. These results are very important because they indicate that the effect of bacterial extract on IgG levels is independent of the mode of administration.

Figure 6:
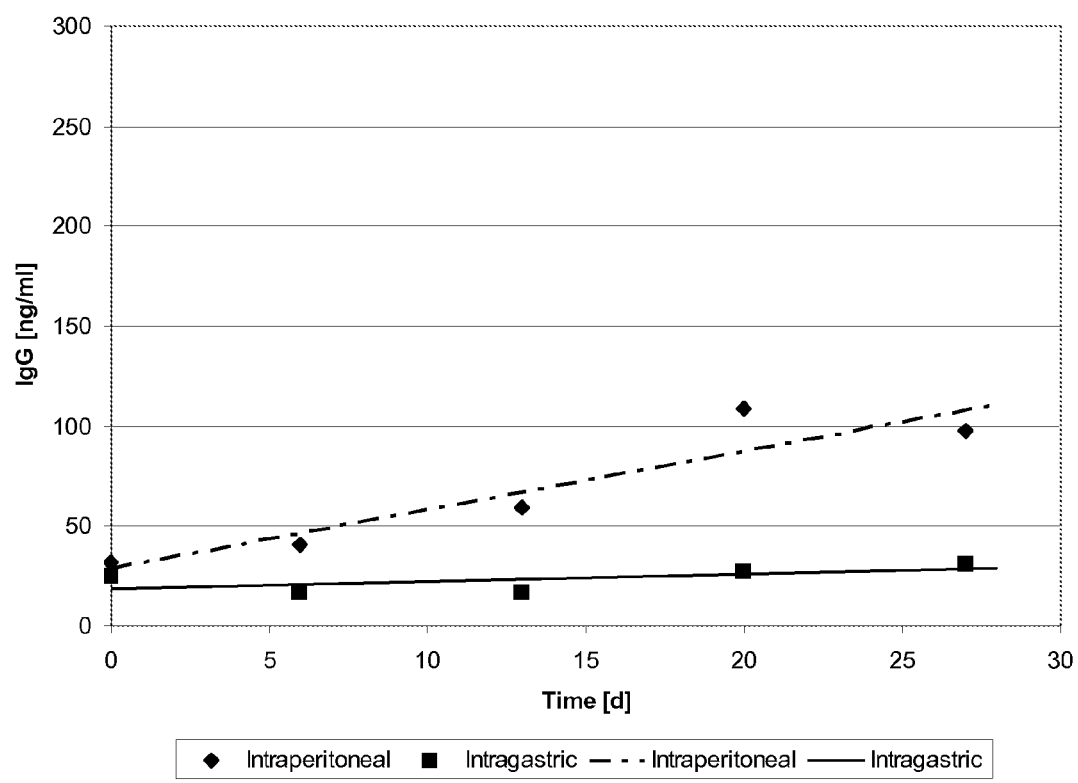

Group Treated with Bacterial Extract+hLf (FIG. 6)

As for the animals undergoing treatment with Bacterial Extract+hLf, two basic facts should be noted. First of all, we can observe that the IgG do not significantly vary from the levels detected in the control group, independently of the mode of administration used. On the other hand, the IgG levels detected at every study time do not reach the levels expected based on the effect of the bacterial extract either with intraperitoneal or intragastric administration.

Comparative Analysis of IgG Levels Among the Various Groups

Intraperitoneal Administration

Control Vs. Bacterial Extract Group:

When we compare the IgG levels of the control group with those found in the group that underwent treatment with bacterial extract, we see a statistically significant increase in the latter group starting on the 6th day after the first administration of bacterial lysate ($p<0.001$). These differences are maintained at all time until completing the study at day 27.

Control Group vs. hLf Group:

With intraperitoneal administration, we saw no statistically significant difference ($p>0.05$) between the IgG levels of the rats that underwent treatment with hLF and those found in the control group at any of the study times.

Control Group Vs hLf+Bacterial Extract Group:

We saw no statistically significant difference ($p>0.05$) between the IgG levels of the rats that underwent conjugated treatment with hLF+bacterial lysate and those found in the control group at any of the study times.

Bacterial Extract Group Vs. hLf Group:

The IgG levels found in the rats that underwent treatment with the bacterial extract alone are significantly higher ($p<0.001$) than the IgG levels found in the animals that underwent treatment with hLF alone from the first days (6 d) until the completion of the study at the 27th day after the first administration.

Bacterial Extract Group Vs. hLf+Bacterial Extract Group:

The IgG levels found in the rats that underwent treatment with the bacterial extract alone are significantly higher ($p<0.001$) than the IgG levels found in the animals that underwent combined treatment with hLF and bacterial extract at all study times after the first administration.

hLf Group Vs. hLf+Bacterial Extract Group:

No statistically significant differences were found ($p>0.005$) between the IgG levels of the rats that underwent treatment with hLf and those detected in the animals that underwent combined treatment with hLf+bacterial extract. This suggests that there must be a protecting effect of hLf that masks the effect of treatment with bacterial extract.

Intragastric Administration

When the various treatments are administered intragastrically, the results are similar to those described in intraperitoneal administration; however, we found a few small differences between both modes of administration. In this case, the differences with regard to the IgG levels detected in the animals treated with the bacterial extract and the rest of the groups (ctrl, hLf, hLf+extract) begin to be statistically significant ($p<0.001$) starting from day 13 after the start of treatment instead of day 6, as occurred when the intraperitoneal mode of administration was used, i.e., there appears to be a slight delay in the immune response in intragastric administration. On the other hand, we see significant differences on day 6 of the study between the group of animals undergoing treatment with hLf and the group of animals undergoing treatment with hLf+extract, with superior IgG levels in the hLf group.

Example 2

3 different classes of cell-culture and blood derived naturally glycosylated proteins were mixed together in a native, that is, physiologically similar standard electrolyte buffer with the concentration shown in the Table with the same 22-mer of the human-lactoferrin peptides described above (using Sequence KCFQWQRNMRKVRGPPVSCIKR (SEQ ID NO: 1)).

An immediate measurement of the change in diffusion cinetics with a standard time-correlation-confocal microscope set-up using fluorescent labels, showed even by low concentration (hLf 94 nM in HBS, 0.1% BSA, 130 nM IgG1) the ease of formulation for all three compound classes by the unspecific moderate binding of the fragment to the examples of therapeutic protein classes including the compound class of example 1.

The column f1 shows without optimization of the experiment the change of an apparent diffusion kinetics accumulated in the channels of the hLf-fragment. The protein I is Albumin a blood protein fraction, known in its recombinant human version or as blood-product, protein II is a selective IgG antibody. Both from commercial sources. hLf as the reference moves as "free" in the volume element of the focus of the microscope whereas about 4% or 15% respectively of the fragment are unspecifically bound and moves slower. Indicating that a supramolecular aggregate of the hLf-fragment is materialized in the sample formulation.

TABLE 4

| | TauT1 (us) | A1 = T/ (1 − T) | TauT2 (us) | A2 = T/ (1 − T) | TauD1 (us) | f1(%) | TauD2 (us) | N(#) | s = z0/w0 | CPS |
|---|---|---|---|---|---|---|---|---|---|---|
| hlf-BSA | 2.91491 | 0.185 | 1 | 0 | 35 | 85 | 244 | 1.4704 | 4.96004 | 7442 |
| hlf-IgG | 2.91491 | 0.185 | 1 | 0 | 33 | 96 | 382 | 0.6862 | 4.96004 | 3072 |
| hlf-pep | 2.91491 | 0.185 | 1 | 0 | 33 | 99 | 1419 | 0.5912 | 4.96004 | 2963 |

LIST OF FIGURES

FIG. 1: Diameter of particles measured with zetasizer

FIG. 2: Zeta potential of particles measured with zetasizer

FIG. 3: IGG-level in control group

Figure 4:
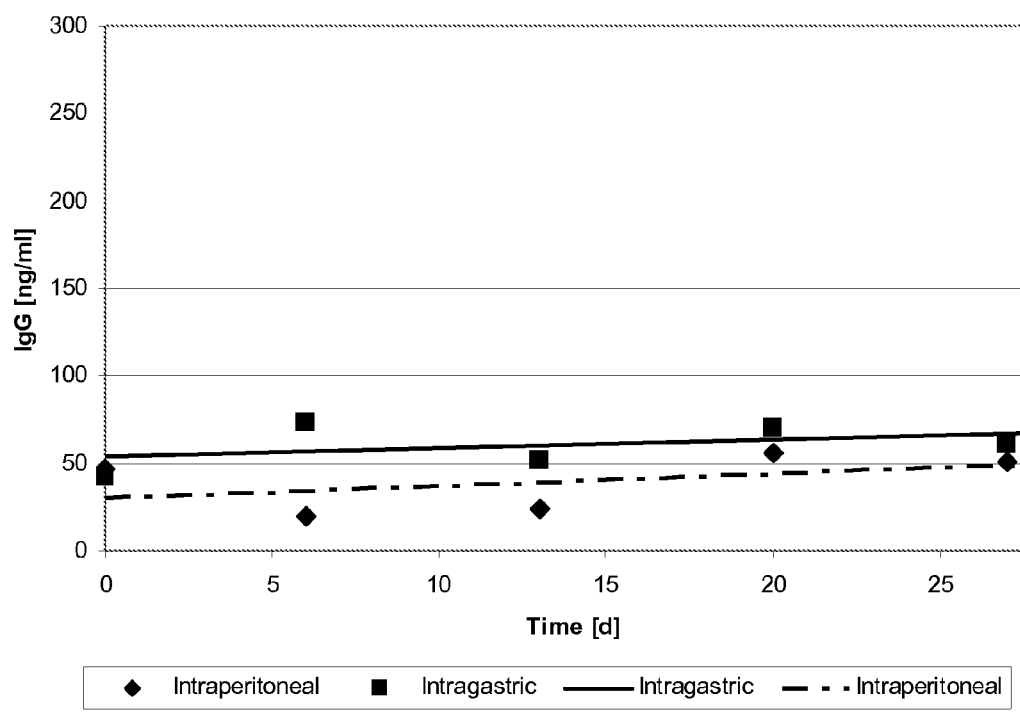

FIG. 4: IgG-level in groups treated with "B"-Formulation (hLf)

Figure 5:
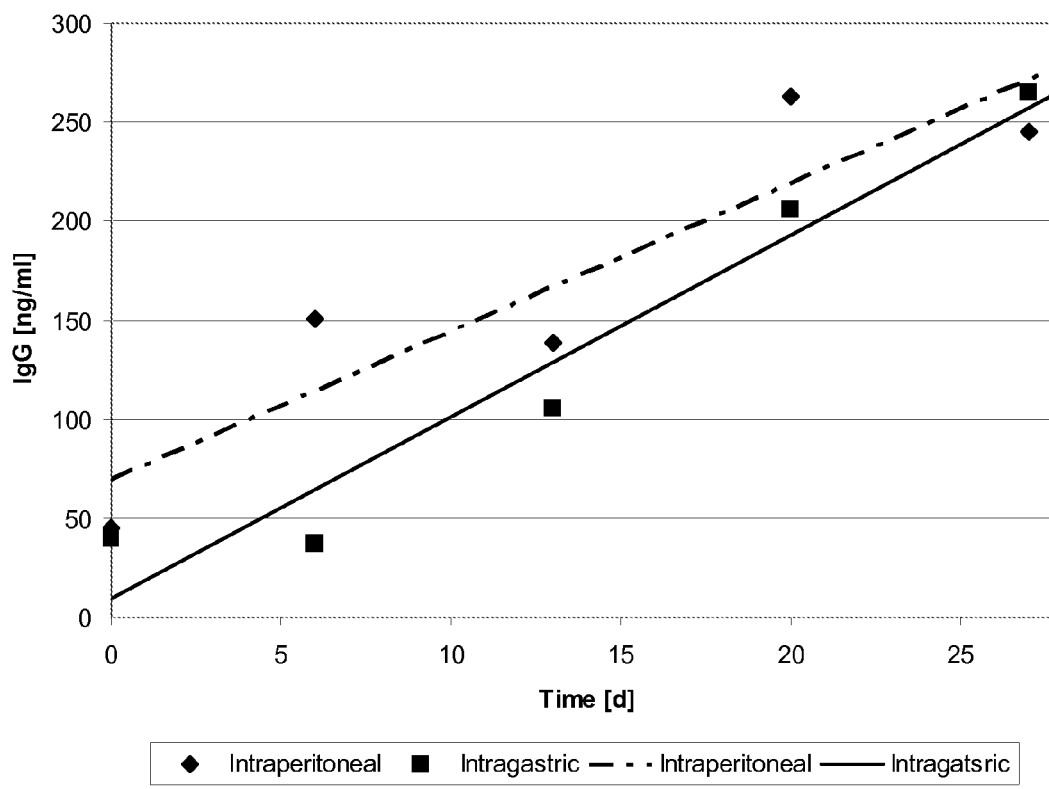

FIG. 5: IgG-level in groups treated with "A"-Formulation (bacterial lysates)

FIG. 6: IgG-level in groups treated with "A+B"-Formulation (bacterial lysates+hLf)

The invention claimed is:

1. A pharmaceutical composition, comprising:
a supramolecular aggregate of a biological active substance and a human lactoferrin derived peptide,
wherein the human lactoferrin derived peptide consists of the amino acid sequence of KCFQWQRNMRKVRG-PPVSCIKR (SEQ ID NO: 1) or a sequence which is at least 90% homologous to SEQ ID NO: 1,
wherein the biological active substance induces an undesired immune response by a mammalian organism, with an effect that after delivery of the pharmaceutical composition to the mammalian organism, there is no or only a diminished induction of the undesired immune response against the biological active substance, and
wherein the biological active substance is in a sample of blood which is transfused to the mammalian organism.

2. The composition according to claim 1, wherein the human lactoferrin derived peptide consists of a sequence that is at least 90% homologous to SEQ ID NO: 1, and cysteine residues in positions 2 and 19 are present.

3. The composition according to claim 2, wherein the undesired immune response is an IgG immune response.

4. The composition according to claim 2, wherein the undesired immune response is an IgE immune response.

5. The composition according to claim 2, wherein the biological active substance is selected from the group consisting of a biological active protein, a biological active peptide, an antisera antibody, a polyclonal antibody, and a monoclonal antibody.

6. The composition according to claim 1, wherein the undesired immune response is an IgG immune response.

7. The composition according to claim 6, wherein the biological active substance is selected from the group consisting of a biological active protein, a biological active peptide, an antisera antibody, a polyclonal antibody, and a monoclonal antibody.

8. The composition according to claim 1, wherein the undesired immune response is an IgE immune response.

9. The composition according to claim 1, wherein the biological active substance is selected from the group consisting of a biological active protein, a biological active peptide, an antisera antibody, a polyclonal antibody, and a monoclonal antibody.

10. The composition according to claim 1, wherein the biological active substance is in or on a surface of an organ which is transplanted to the mammalian organism.

11. The composition according to claim 1, wherein the biological active substance and the human lactoferrin derived peptide are not covalently bound to each other in the supramolecular aggregate.

12. The composition according to claim 1, wherein the biological active substance and the human lactoferrin derived peptide are covalently bound to each other in the supramolecular aggregate.

13. The composition according to claim 1, wherein the human lactoferrin derived peptide consists of the amino acid sequence of SEQ ID NO: 1 or a sequence which is at least 95% homologous to SEQ ID NO: 1.

14. A pharmaceutical composition, comprising:
a supramolecular aggregate of a biological active substance and a human lactoferrin derived peptide,
wherein the human lactoferrin derived peptide consists of the amino acid sequence of KCFQWQRNMRKVRG-PPVSCIKR (SEQ ID NO: 1) or a sequence which is at least 90% homologous to SEQ ID NO: 1,
wherein the biological active substance induces an undesired immune response by a mammalian organism, with an effect that after delivery of the pharmaceutical composition to the mammalian organism, there is no or only a diminished induction of the undesired immune response against the biological active substance, and
wherein the biological active substance is in or on a surface of an organ which is transplanted to the mammalian organism.

15. The composition according to claim 14, wherein the human lactoferrin derived peptide consists of the amino acid sequence of SEQ ID NO: 1 or a sequence which is at least 95% homologous to SEQ ID NO: 1.

\* \* \* \* \*